United States Patent [19]

Trani et al.

[11] Patent Number: 5,118,705
[45] Date of Patent: Jun. 2, 1992

[54] WATER SOLUBLE SALTS OF PURPUROMYCIN AND PHARMACEUTICAL FORMULATIONS THEREOF

[75] Inventors: Aldo Trani; Sergio Bellini, Carate Brianza; Beth P. Goldstein, Milan; Luigi Simioni, Cusano Milanino, all of Italy

[73] Assignee: Gruppo Lepetit S.p.A., Milan, Italy

[21] Appl. No.: 660,482

[22] Filed: Feb. 25, 1991

[30] Foreign Application Priority Data

Feb. 28, 1990 [EP] European Pat. Off. ............ 90103846

[51] Int. Cl.⁵ .................... A61K 31/35; C07D 307/92
[52] U.S. Cl. .................... 514/455; 549/264
[58] Field of Search .................... 549/264; 514/455

[56] References Cited

U.S. PATENT DOCUMENTS

| 2,973,357 | 2/1961 | Johnson et al. | 549/264 |
| 3,000,882 | 9/1961 | Wettstein et al. | 549/264 |
| 3,914,257 | 10/1975 | Pagani et al. | 549/264 |
| 4,229,466 | 10/1980 | Miyazaki et al. | 549/264 |

Primary Examiner—C. Warren Ivy
Assistant Examiner—Amelia A. Owens
Attorney, Agent, or Firm—J. Michael Dixon

[57] ABSTRACT

Water soluble salts of purpuromycin, their use for the topical treatment of infectious vaginitis and topical dosage forms containing said products. Oral and parenteral formulations for administration of the water soluble purpuromycin salts. The water soluble salts of purpuromycin are simultaneously active against the main causative agents of infectious vaginitis i.e.: *Candida vaginalis*, *Trichomonas vaginalis* and *Gardnerella vaginalis*.

17 Claims, No Drawings

WATER SOLUBLE SALTS OF PURPUROMYCIN AND PHARMACEUTICAL FORMULATIONS THEREOF

This invention concerns water soluble salts of the antibiotic purpuromycin which are useful medicaments for topical, oral and parenteral treatment of microbial infections and pharmaceutical formulations of said salts particularly useful for such use.

In this description and claims the term "water soluble" is intended to mean that the solubility of the product in water at room temperature permits preparation of an aqueous solution containing purpuromycin in a sufficient concentration and at a pH value such that it may be antimicrobially effective when administered to patient in a volume compatible with the usual pharmaceutical practice. More particularly, the term "water soluble" when used here in relation to a purpuromycin salts identifies purpuromycin salts with bases that are soluble in water at room temperature at a concentration of at least 1 mg/ml and at a physiologically acceptable pH, which, in any case, should be lower than 9; otherwise the purpuromycin moiety undergoes a degradation process. The term "patient" used herein is taken to mean mammals such as primate (including humans, sheep, horses, cattle, dogs, cats, rats, mice), and birds.

The salts of this invention are addition salts of purpuromycin with organic amines which are pharmaceutically acceptable and form with purpuromycin salts which are water soluble and whose stability in aqueous solution may satisfy the usual requirements for the manufacture and use of pharmaceutical formulations containing water. Such organic amines are generally selected from (a) mono-, di-, and tri-($C_2$-$C_5$) alkyl amines wherein the alkyl group contains at least one hydrophylic substituent selected from OH, SH and $NH_2$ and whose pK value is comprised between 8 and 9.5 and (b) basic amino acids having a $pK_3$ value between 10 and 11.

The above pK values refer to the dissociation constants of the conjugate acids of the amine or basic amino acids in water at room temperature. If desired, the corresponding values of the basic dissociation constants ($pK_b$) can be easily calculated by using the expression $pK_b = 14-pK$.

The index "3" of the above term "$pK_3$" indicates that the respective value refers to the ionization constant of the conjugate acid of the second basic group (e.g.: the second amino group). Purpuromycin is an antibiotic produced by *Actinoplanes ianthinogenes* nov. sp. A/1668 which was original deposited at the American Type Culture Collection (ATCC) of Rockville, Md. 20852 USA on Jan. 29, 1973 with the number 21884. This strain was accepted under the conditions prescribed by the Budapest Treaty as of Jan. 31, 1981.

Purpuromycin is represented by the following general formula:

Its preparation is described in UK Patent 1455128 and U.S. Pat. No. 3,914,257, wherein is also reported its antimicrobial activity. Accordingly, purpuromycin is shown to be active in vitro against both Gram-positive and Gram-negative bacteria and fungi, including filamentous fungi (e.g., *Trichophyton mentagrophytes*) and yeasts e.g., *Candida albicans*). In the prior art, no indication is given about the activity of purpuromycin against *Trichomonas vaginalis* and against *Gardnerella vaginalis* and other anaerobic bacteria which are known to be, besides *Candida albicans*, the main causative agents of infectious vaginitis.

Infectious vaginitis is mainly due to the unbalanced presence in the vagina of fungi, protozoa and bacteria. Several authors have extensively discussed the problem in the medical literature and a complete review on the pathogenesis and treatment of said infections was published by L. V. H. Hill and J. A. Embil in Can. Med. Assoc. J. Vol. 134, pag. 321-331 (1986). Fungal vaginitis is essentially due to the yeast *Candida albicans*. Synthetic imidazoles (e.g. miconozole, econozole, clotrimazole, ketoconozole) and triazoles (e.g. fluconazole), gentian violet, candicidin, amphotericin and nystatin have been described as effective against *Candida albicans* infections. Topically administered nystatin is considered to be the most useful drug for combatting or preventing yeast vaginitis.

Protozoal infections are essentially due to *Trichomonas vaginalis*. Nitroimidazoles (e.g. metronidazole and tinidazole) are active against *Trichomonos vaginalis*. Orally administered metronidazole is recommended for the treatment of said infection although with some important drawbacks due to potential mutagenic and carcinogenic effects which , limits its application in pregnant patients (see: D. A. Eschenback, Clin. Obstet. Gynecol. 26 (1), 186-202, 83).

Vaginitis caused by neither Trichomonas nor yeasts is generally defined as nonspecific vaginitis or bacterial vaginitis and is generally due to bacteria, in particular *Gardnerella vaginalis*. Anaerobic bacteria (Bacteroides spp., Peptococcus spp., comma-shaped bacteria) are also frequently present in nonspecific vaginitis (A. Skarin et al. Scand. J. Infect. Dis. Suppl. 40, 81-84, 1983; E. E. Petersen et al., Scand.J. Infect. Dis. Suppl. 40, 97-99, 1983). Although several antibiotics and synthetic antibacterials are active against *Gardnerella vaginalis* and the other above mentioned bacteria, administration of metronidazole is the most commonly recommended form of therapy for nonspecific vaginitis. Simultaneous presence of Gardnerella and other anaerobes in trichomonal infections has often been demonstrated. (C. A. Ison et al.: J. Clin. Pathol. Vol. 36, 1367-1370, 1983). As metronidazole is active against both Trichomonas and *Gardnerella vaginalis*, this justifies the wide use of metronidazole in the therapy of both trichomoniasis and nonspecific vaginitis.

However, metronidazole is not active against yeasts and development of yeast vaginitis has been observed

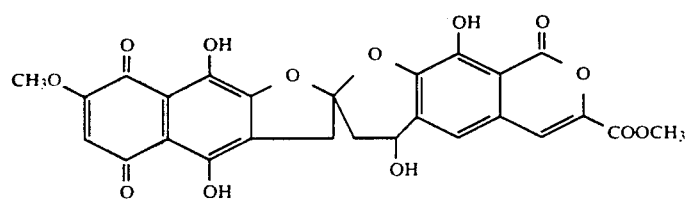

under metronidazole treatment (see: F. Fleury, Chemotherapy 28 (suppl. 1), 48–50, 1982). Moreover, strains of *Gardnerella vaginalis* resistant to metronidazole have been isolated (see Table III hereinbelow). To the best knowledge of the inventors, the substances which have been indicated as suitable for the therapy or prevention of each of the three types of infectious vaginitis are not simultaneously effective against Trichomonas, Candida and Gardnerella.

One of the main objects of this invention is to provide water soluble salts of purpuromycin which are simultaneously active against all three above mentioned pathogenic microorganisms and can be advantageously employed in the treatment of infectious vaginitis. Accordingly, a further object of this invention is the use of water soluble salts of purpuromycin in a method and topical dosage forms for the topical treatment of vaginal infections.

In view of the simultaneous activity against *Candida vaginalis*, *Trichomonas vaginalis* and *Gardnerella vaginalis*, the water soluble purpuromycin salts, their use in a method of treatment and their topical dosage forms are particularly suitable for the treatment of patients affected by infectious vaginitis when the causative agents of said infection are not or cannot be unequivocally determined or there is evidence or likelihood of the contemporaneous presence of at least two of the above mentioned pathogenic organisms.

Although good medical practice would prescribe that the diagnosis of infectious vaginitis be supported by etiological determinations, common medical practice, economic, logistic and environmental factors lead to a practical situation in which most of the diagnosis of infectious vaginitis are based only on the symptomatology of the patient. Examination of vaginal smears and microbiological tests are usually carried out only in those cases where the intervention of a specialist is involved because of inefficacy of the therapy or recurrence of the infection.

Therefore, a medicament which is simultaneously active against all three main causative agents of infectious vaginitis represents valuable progress in the treatment of such disease.

The pharmaceutically acceptable water soluble salts of purpuromycin which form the main object of this invention are formed with amines which impart the desired solubility without modifying the molecular structure of the antibiotic or negatively affecting its stability.

In fact, the complete salification of at least one of the three phenolic hydroxy groups of the purpuromycin moiety with alkali metal cations, or organic cations of strong organic bases (e.g. showing pK values higher than 9.5) implies establishing conditions which provoke the degradation of the purpuromycin substrate. For instance, alkali metal hydroxydes (e.g. NaOH) alkali metal carbonates (e.g. $Na_2CO_3$), mono-, di- and tri-lower alkyl amines provoke hydrolysis of the carbomethoxy group of purpuromycin leading to an almost inactive carboxylic acid derivative. On the other hand, weak bases cannot form stable enough water soluble salts with purpuromycin since its phenolic groups do not possess sufficient acid strength to promote complete salification. For instance, sodium bicarbonate or organic bases with a pK value lower than 8 (e.g.: pyridine, aniline, anisidine, N,N-dimethylaniline) do not have sufficient basic strength to salify the phenolic hydroxy group.

Other organic amines which may have a pK value falling within the appropriate interval (e.g. benzyl amine),do not possess sufficient hydrophilic character to impart the desired solubility to the respective purpuromycin salts. Similar considerations apply to amino acids showing insufficient basicity (e.g. those amino acids which do not possess a second aminic function) or, alternatively, basic amino acids bearing such basic function which imparts a too high $pK_3$ value. For instance, arginine ($pK_3$ value higher than 13) form salts which are not sufficiently stable because of the partial degradation of the purpuromycin moiety promoted by the strong basicity of the arginine cation while glycine, alanine, valine and threonine cannot form stable salts with purpuromycin because of insufficient basicity.

Branched or linear mono-, di- or trialkylamine wherein the alkyl chain has 2 to 5 carbon and contains at least one hydrophilic substituent selected from OH, SH and $NH_2$ and whose pK value is comprised between 8 and 9.5 and basic natural and synthetic amino acids (e.g. amino acids having an additional amino group), in either L, D or racemic form, having a pK3 value between 10 and 11 may form water soluble salts with purpuromycin according to this invention.

For instance, according to this invention, have been obtained salts of purpuromycin whose solubility in water at room temperature ranges between 2 and 10 mg of purpuromycin per ml at a pH value between 8 and 9. This solubility may be increased by adding an appropriate water miscible organic solvent which can be tolerated up to certain concentration in the pharmaceutical practice (e.g.: dimethylsulfoxide, propylene glycol, polyoxyethylene glycol, polyoxyethylene glycol partially or totally esterified with saturated or unsaturated fatty acids and their mixtures, dimethylisosorbide, polyoxyethylene glycol ethers, e.g. polyoxyethylene glycol tetrahydrofurfuryl ether, and the like).

According to a further object of this invention, said water soluble salts must show characteristics which make them suitable for pharmaceutical application with regard to both stability, tolerability and ability to be formulated into administrable pharmaceutical dosage forms. In other words, they must be pharmaceutically acceptable. Among the organic amines which form water soluble salts according to this invention are, for instance, ethanolamine, diethanolamine, tris (hydroxymethyl) aminomethane (TRIS), and L-lysine.

Purpuromycin usually forms salts with the appropriate organic amine in a ratio 1:1 and 1:2. According to this invention, the inventors have isolated also salts with a purpuromycin:amine 1:1.5 ratio which are particularly stable. The water soluble salts of purpuromycin of this invention are prepared by dissolving purpuromycin in a suitable organic solvent mixable with water which is capable of dissolving purpuromycin and whose complete elimination from the recovered solid salt does not raise particular difficulties (e.g. tetrahydrofuran, dioxane).To said solution a water or lower alkanol (e.g. methanol; ethanol) solution or a mixture thereof containing the appropriate amine in the appropriate molecular proportion is added. The molecular proportion is calculated with respect to the desired ratio between purpuromycin and the amine (1:1, 1:1.5 or 1:2). Both solutions are prepared by dissolving the reactants with stirring and raising the temperature, if necessary, from the room temperature to a temperature which is sufficient to bring all solids into solution. In general, the temperature of the solutions ranges from 20° C. to 60°

C. When the addition of the amine solution to the purpuromycin solution is complete, the reaction mixture is stirred for 10 to 40 minutes and then it is evaporated to dryness under reduced pressure at a temperature between the room temperature and 60° C. The residue is then washed with an aprotic organic solvent in which the salt is insoluble such as, for example, diethyl ether.

If the residue from a preparation of the 1:2 salt is repeatedly washed with the aprotic solvent, it loses a part of the salified amine to yield a 1:1.5 salt.

The water soluble salts of purpuromycin of this invention have the same biological activity as purpuromycin and, moreover, show more favorable characteristics for formulation in suitable pharmaceutical dosage forms for the treatment of infectious vaginitis.

Since the equivalency of the microbiological activity of purpuromycin and its water soluble salts against the sensitive microorganisms has been demonstrated through a series of test in vitro, (see TABLE I), all representative microbiological data shown in this description, when referring to purpuromycin alone, are to be considered as obtained with a water soluble salt of purpuromycin of this invention.

Sabouraud-dextrose broth (*Trichophyton mentagrophytes*). Inocula were approximately $10^4$ CFU/ml.

b) *Trichomonas vaginalis*

MIC were performed in flat-bottomed microtiter trays, with 0.2 ml per well. The medium was TYM modified basal medium (Merck) plus 10% horse serum (treated to inactivate complement). The inoculum was ca. $10^5$ organisms/ml; incubation was for 48 h in an anaerobic hood (37° C.). The microtiter wells were read using an inverted light microscope. The MIC was taken as the lowest concentration at which no live (mobile) protozoa were seen.

c) *Gardnerella vaginalis*

MIC were determined with an agar dilution method in Casman medium base (Difco) plus 5% (v/v) rabbit blood and 0.15% (v/v) lysed rabbit blood. Incubation was for 48 h in an anaerobic hood (37° C.); inoculum ca. $10^5$ CFU.

To further illustrate the newly discovered utility of purpuromycin water soluble salts against *Trichomonas vaginalis* representative comparison tests with other

TABLE I

In vitro activity of purpuromycin water soluble salts and purpuromycin

| Strain | M.I.C. (mg/l) | | |
|---|---|---|---|
| | Purpuromycin salt with L-lysine (1:1.5)* | Purpuromycin salt with TRIS (1:1.5)* | Purpuromycin |
| *Staph. aureus* Tour I 165 | 0.06 | 0.06 | 0.06 |
| *Staph. epidermidis* ATCC 12228 | 0.06 | 0.06 | 0.06 |
| *Staph. haemolyticus* L 602 | 0.06 | 0.06 | 0.06 |
| *Strep. pyogenes* L 49 | 0.06 | 0.06 | 0.06 |
| *Strep. pneumoniae* L 44 | 0.13 | 0.13 | 0.06 |
| *Enterococcus faecalis* ATCC 7080 | 0.06 | 0.06 | 0.06 |
| *Propionibacterium acnes* ATCC 6919 | 0.06 | 0.06 | 0.06 |
| *Bacteroides fragilis* ATCC 23745 | 0.13 | 0.13 | 0.13 |
| *Neisseria gonorrhoeae* L 997 | 0.06 | 0.06 | 0.06 |
| *Haemophilus influenzae* ATCC 19418 | 0.13 | 0.06 | 0.06 |
| *Escherichia coli* SKF 12140 | 32 | 16 | 8 |
| *Candida albicans* SKF 2270 | 1 | 1 | 1 |
| *Trichophyton mentagrophytes* SKF 17410 | 1 | 1 | 1 |
| *Trichomonas vaginalis* TVL | 4 | 4 | 4 |
| *Gardnerella vaginalis*** | 16 | 16 | 16 |

*calculated as weight of purpuromycin
**The assay was carried out on strain ATCC 14018 and 10 clinical isolates (L 529, L 530, L 531, L 1622, L 1623, L 1624, L 1626, L 1627, L 1628, L 1629) all strains showed the same M.I.C. value Conditions for Table I a) All microorganisms except *Trichomonas vaginalis* and *Gardnerella vaginalis*

MIC were determined by the microbroth dilution test. Bacteria were grown at 37° C., fungi at 30° C. Incubation was for 20 h, except for *Propionibacterium acnes, Bacteroides fragilis, Neisseria gonorrhoeae, Haemophilus influenzae* (48 h) and *Trichophyton mentagrophytes* (72h) *Neisseria gonorrhoeae* and *Haemophilus influenzae* were incubated in a $CO_2$-enriched (5%) atmosphere; *Propionibacterium acnes* and *Bacteroides fragilis* in an anaerobic hood.

Media used were: Oxoid Iso-sensitest broth (Staphylococci, *Enterococcus faecalis* and *Escherichia coli*); Difco Todd-Hewitt broth (streptococci); Difco GC base broth with 1% BBL IsoVitaleX (*Neisseria gonorrhoeae*); Difco Brain-Heart Infusion broth with 1% Difco supplement C (*Haemophilus influenzae*); Difco Wilkins-Chalgren broth (*Propionibacterium acnes* and *Bacteroides fragilis*); Difco Yeast Nitrogen Base broth with 1.5 g/l asparagine (*Candida albicans*); Difco known antifungal agents have been carried out by the two-fold tube dilution method. *Trichomonas vaginalis* (applicant's internal code TVL) was grown on Trichomonas Culture Medium Base (Merck) plus 10% heat treated horse serum. Inoculum: approximately $10^5$ organisms/ml. Incubation: 48 hours at 37° C. Purpuromycin was dissolved in dimethylsulfoxide (DMSO) at a concentration of 5 mg/ml and added to the culture medium at the maximum concentration of 128 microgram/ml. Under these conditions purpuromycin showed a minimal inhibitory concentration (M.I.C.) value against *Trichomonas vaginalis* strain TVL (applicant's internal code) of 4 micrograms/ml.

The comparative experiments with other known antifungal agents showed that usually their activity against *Trichomonas vaginalis* strain TVL is very low or negligible as indicated in the following TABLE II.

TABLE II

Activity of purpuromycin, various antifungal agents and metronidazole against *Trichomonas vaginalis* strain TVL

| COMPOUND | MIC (mcg/ml) |
|---|---|
| Purpuromycin | 4 |
| Amphotericin B | 64 |
| Nystatin | >128 |
| Miconazole | 32 |
| Clotrimazole | 64 |
| Ketoconazole | >128 |
| Metronidazole (positive control) | 0.25 |

The activity of purpuromycin water soluble salts against *Gardnerella vaginalis* ATCC 14018 and other 11 clinical isolates (identified with applicant's internal codes: L 531, L 1622, L 1623, L 1624, L 1625, L 1626, L 1627, L 1628, L 1629, L 1630, L 1631) have also been compared with those of other known antifungal and antiprotozoal agents by standard two fold dilution methods. The strains were grown on Casman medium (Difco) plus 5% (v/v) whole rabbit blood and 0.15 (v/v) lysed rabbit blood. Inoculum size: approximately $10^4$ colony forming units per spot. Incubation in an anaerobic hood: 48 hours at 37° C.

The data reported in TABLE III show that purpuromycin water soluble salts inhibit the growth of all tested strains at a concentration of 8 micrograms/ml, while the other antifungal or antiprotozoal agents in most cases have lower or negligible activity. It is noteworthy that purpuromycin salts are active also on strains resistant to metronidazole (MIC >32 micrograms/ml), nystatin (MIC >128 micrograms/ml) and miconazole (MIC >128 micrograms/ml).

TABLE III

Activity of purpuromycin, other antifungal and antiprotozoal agents against *Gardnerella vaginalis*

| COMPOUND | NUMBER OF STRAINS WITH MIC OF | | | | | |
|---|---|---|---|---|---|---|
| | 4 | 8 | 16 | 32 | 64 | 128 >128 (mcg/ml) |
| Purpuromycin | | 12 | | | | |
| Metronidazole | 1 | 3 | 4 | | 1 | 3 |
| Nystatin | | | | | | 12 |
| Clotrimazole | | 2 | 1 | 2 | 5 | 2 |
| Miconazole | 1 | 7 | | 2 | | 2 |

The activity of purpuromycin water soluble salts against yeasts was confirmed through experiments carried out with *Candida albicans* ATCC 10231, *Candida albicans* SKF 2270 and 19 clinical isolates (applicant's internal code L 1404, L 1405, L 1406, L 1407, L 1408, L 1409, L 1410, L 1411, L 1412, L 1413, L 1414, L 1415, L 1416, L 1417, L 1418, L 1429, L 1430, L 1431, L 1432).

This set of experiments included also one strain each of two other Candida species, *Candida tropicalis* and *Candida kruzei*. The M.I.C. were determined by the two-fold dilution method in buffered (0.01 M phosphate buffer, pH 7.4) yeast nitrogen base medium (Difco) supplemented with 1.5 g/liter asparagine in microtiter trays. Inocula were approximately $10^4$ colony forming units/ml. Incubation was for 20 h at 30° C. Purpuromycin was dissolved in DMSO and added to the cultures as above. The following TABLE IV reports the MIC values for the whole set of strains.

TABLE IV

Activity of purpuromycin against Candida strains

| Species (number of strains) | MIC (micrograms/ml) |
|---|---|
| *Candida albicans* (19 clinical isolates, MIC range) | 1–4 |
| *Candida albicans* SKF 2270 | 1 |
| *Candida albicans* ATCC 10231 | 0.5 |
| *Candida tropicalis* L 243 | 2 |
| *Candida kruzei* L 244 | 4 |

In comparative tests a series of antibacterial agents (penicillin G, ampicillin, cefalexin, cefoxitin, cephaloridine, clindamycin, erythromycin, chloramphenicol, tetracycline, gentamicin, spectinomycin, metronidazole, sulfamethoxazole) which are known to be active against *Gardnerella vaginalis* (see: S. Shanker et al.: Eur. J. Clin. Microbiol., October 1982, 298–300) showed in all cases M.I.C. values higher than 128 microgram/ml, against both *Candida albicans* SKF 2270 and *Candida albicans* ATCC . 10231.

The effectiveness of the water soluble salts of purpuromycin in the topical treatment of yeast vaginal infection was also tested in ovariectomized rats (Charles River) treated subcutaneously with 4 mg of estradiol benzoate approximately two weeks after ovariectomy. Five days later they were inoculated intravaginally with approximately $5 \times 10^6$ colony forming units (CFU) of *Candida albicans* strain SKF 2270 in 25 microliters of Nutrient Broth (no.2, Oxoid) containing 15% (vol/vol) of glycerol. Topical intravaginal therapy was twice daily for three days, starting one day after infection, with 100 microliters of a water soluble salt of purpuromycin suspension in a mixture of 10:90 DMSO-polyethylene glycol 400, corresponding to 2 or 5 mg/rat/treatment. The day after the last treatment, vaginal smear samples (calibrated 10 microliter loops) were diluted and plated for viable organism counts on Sabouraud agar (Difco). Each group contained 10 animals. As can be seen from the Table V, animals treated with purpuromycin salts with L-lysine had significantly reduced numbers of viable yeasts cell/sample.

TABLE V

Topical antifungal activity of water soluble salts of purpuromycin in rats

| Group | Treatment | Mean $\log_{10}$CFU/smear sample $\pm$ SD |
|---|---|---|
| 1 | vehicle | 3.87 ± 0.50 |
| 2 | Purpuromycin 1:1.5 L-lysine salt (2 mg) | 2.60 ± 0.49* |

*P < 0.01 vs group 1 controls
CFU = colony forming unit
SD = standard deviation

The above findings make the pharmaceutically acceptable water soluble salts of purpuromycin of this invention particularly suitable for the treatment of vaginal infections. Accordingly, one of the objects of this invention is to provide a method for combatting and/or preventing vaginal infections caused by fungi, protozoa, and bacteria, in particular, *Candida albicans*, *Trichomonas vaginalis* and *Gardnerella vaginalis*, which comprises topically administering to the patient in need thereof an amount of water soluble purpuromycin salt capable of inhibiting the growth of the above mentioned microorganisms.

According to the most recent views of the chemotherapy of vaginal infections, the patients in need of said treatment may be both the female affected by the infection and, in the case of chronic recurrent infections, also her male sexual partner. A further object of this invention is to provide pharmaceutical dosage forms particularly useful for the topical administration of the pharmaceutically acceptable water soluble salts of purpuromycin in the treatment of vaginal infections. As purpuromycin is a solid practically insoluble in water and in lower alkanols, the preparation of topical dosage forms suitable for the treatment of infectious vaginitis is a problem requiring specific solutions. According to this invention purpuromycin derivatives which can be easily formulated into topical dosage forms are provided including vaginal tablets, pessaries, creams, ointments, gels, suppositories, lotions, foams, powder, suspensions, drug delivery systems and the like which permit delivery and release of the active substance into the infection sites.

The pharmaceutical topical dosage forms can be prepared both in anhydrous and aqueous bases and contain a water soluble salt of purpuromycin and one or more excipients such as for example: starch, lactose, glucose, talc, cellulose, for solid dosage forms; methocel, modified vegetable oils, mineral oils, polyalkylene glycols, fatty acids and alcohols, polyethylene glycol fatty acids esters and the like for semi-solid dosage forms; water, alkanols, glycerol, lanolin, polyethylene glycols, mineral oil, pharmaceutically acceptable organic solvents (e.g. DMSO, methyl-decyl-sulfoxide) and the like for liquid or semi-liquid dosage form. The dosage forms may optionally contain other active ingredients or ingredients which preserve and favor the antimicrobial action of purpuromycin in the infection sites (e.g. antiseptics, emulsifiers, surfactants and the like). Useful indications for the preparations of suitable topical dosage forms can be found in: Remington's Pharmaceutical Sciences, 17th Edition, 1985 (Mack Publishing Company, Easton, Penna.).

The purpuromycin water soluble salts are employed either as fine crystalline powder or in micronized form.

Purpuromycin in itself is practically insoluble in water (0.022 mg/ml at pH 8.5 buffer) and is poorly soluble in most organic solvents. Therefore purpuromycin is not suitable for preparing pharmaceutical formulations which contain the active ingredient in at least partially, dissolved form. One of the advantages of the water soluble salts of purpuromycin is that they show more flexibility in the preparation of topical formulations because of their improved solubility in aqueous media which permit utilization of aqueous bases. Even if the basic pH value of such formulations may be neutralized by the acidic pH of the local district where they are applied (e.g. the vagina) and some precipitation of purpuromycin may occur, these formulations, in general, have lower viscosity and favor better contact of the active ingredient with the infected tissue. Moreover, on contact with the acidic pH of the tissutal mucosa the aqueous solutions of purpuromycin salts may yield precipitates of purpuromycin at colloidal state that facilitate spreading the antibiotic on the mucosa and increase its dissolution rate, thus improving its bioavailability.

The amount of active water soluble purpuromycin salts in the finished topical dosage forms depends on the minimal inhibitory concentration of purpuromycin against causative agents of the infection and its particular type of formulation. In the following text, reference is made to purpuromycin alone when defining the dosages, however, it is intended that th corresponding dosage of the respective water soluble salt containing the same amount of purpuromycin should be employed.

The dosage may obviously be adjusted according to the severity of the infection and the type of patient. Experimental tests for determining the sensitivity of the microorganisms isolated from the patient may also offer useful indications in selecting the appropriate dosage. In general terms, the effective dosage ranges between 10 and 600 mg, preferably between 100 and 400 mg, for each vaginal application once to three times daily. The course of treatment may last from 3 to 10 days or longer, if required.

Liquid or semi-liquid dosage forms such as, creams, lotions, ointments, foams and suspensions generally contains from 0.05 to 5 percent by weight of purpuromycin. If necessary, this range may be broadened without any substantial modification of the characteristics of the respective dosage form. Solid intravaginal unit dosage forms such as vaginal tablets and suppositories can be manufactured in different dosages. For instance, they may contain from 10 to 600 mg of purpuromycin. Preferred dosages are comprised between 100 and 400 mg.

Typical drug delivery systems incorporating the water soluble salt of purpuromycin are formulated, for instance, with biodegradable polymers for controlled release such as those described at pages 106-119 of the book: Drug Delivery Systems. Fundamentals and Techniques—Edited by P. Johnson and J. G. Lloyd-Jones, 1987, Ellis Horwood Ltd. Chichester, England.

A further utility of the pharmaceutically acceptable water soluble salts of purpuromycin is for the manufacture of pharmaceutical dosage forms for use in oral and/or parenteral administration against infections due to microorganisms sensitive to purpuromycin.

For oral administration the water soluble salts of purpuromycin can be formulated into solid or liquid preparations such as capsules, pills, tablets, troches, lozenges, melts, powders, solutions, suspensions or emulsions. The solid unit dosage forms can be capsules, which can be of the ordinary hard- or soft-shelled gelatin type containing, for example, surfactants, lubricants, and inert fillers such as lactose, sucrose, calcium phosphate and corn starch. In another embodiment the compounds of this invention can be tableted with conventional tablet bases such as lactose, sucrose, and corn starch in combination with binders such as acacia, cornstarch, or gelatin; disintegrating agents intended to assist the break-up and dissolution of the tablet following administration, such as potato starch, alginic acid, corn starch and guar gum, lubricants intended to improve the flow of tablet granulations and to prevent the adhesion of tablet material to the surfaces of the tablet dies and punches, for example, talc, stearic acid, or magnesium, calcium or zinc stearate; dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

Usually, the oral dosage forms of the water soluble salts of purpuromycin are designed for the administration of an effective dosage ranging from 15 to 600 mg, once to three times daily.

The purpuromycin salts of this invention may also be used for the preparation of pharmaceutical dosage forms to be administered parenterally, that is, subcutaneously, intravenously, intramuscularly or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol or hexadecyl alcohol, glycols such as propylene glycol or polyoxyethylene glycol, glycerol, ketals such as 2,2-dimethyl-1,3-dioxolane-4-methanol, an oil, a fatty acid, a fatty acid ester or glyceride, or an acetylated fatty acid glyceride, with or without the addition of a pharmaceutically acceptable surfactant such as a soap or a detergent, a suspending agent such as pectin, methylcellulose, hydroxypropyl methylcellulose or carboxymethylcellulose, or an emulsifying agent, and other pharmaceutical adjuvants. Illustrative of oils which can be used in the parenteral formulations of this invention are those of petroleum, animal, vegetable, and synthetic origin, for example, peanut oil, soybean oil, sesame oil, cottonseed oil, corn oil, olive oil, petrolatum and mineral oil. Suitable fatty acids include oleic acid, stearic acid, and isostearic acid. Suitable fatty acid esters are, for example, ethyl oleate and isopropyl myristate. Suitable soaps include fatty acids alkali metal, ammonium, and triethanolamine salts; suitable detergents include cationic detergents, for example, dimethyl dialkyl ammonium halides; alkyl pyridinium halides, and alkylamine acetates, anionic detergents, for example, alkyl, aryl, and olefin sulfonates, alkyl olefin, ether and monoglyceride sulfates, and sulfosuccinates; non ionic detergents, for example, fatty amine oxides, fatty acid alkanolamides, and polyoxyethylene-polypropylene copolymers; and amphoteric detergents, for example, alkyl beta-aminoproprionates and 2-alkylimidazoline quarternary ammonium salts, as well as mixtures. Preservatives and buffers may also be used advantageously. In order to minimize or eliminate irritation at the site of injection, such compositions may contain a non-ionic surfactant having a hYdrophile-liphophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyoxyethylene sorbitan fatty acid esters.

In all above cases the final solution or suspension must show a pH value which is compatible with the stability of the purpuromycin salts and therefore the addition of soaps, detergents, surfactants and the like must made in such a way and amounts that it does not bring the pH at an undesired value.

Usually, the parenteral unit dosage form of the water soluble salts of purpuromycin are designed for the administration of an effective dosage ranging from 5 to 300 mg once to three times daily. The parenteral composition of this invention typically contain the water soluble salts of purpuromycin in solution. Preferably, said solutions are prepared from lyophylized purpuromycin water soluble salts and the appropriate solvent or diluent just before administration.

EXAMPLES

The following examples show the preparation of some water soluble salts of purpuromycin and some pharmaceutical formulations suitable for their administration.

EXAMPLE 1

Salt of purpuromycin with tris-(hydroxymethyl) aminomethane

Purpuromycin (840 mg., 1.56 mmole) is dissolved with stirring under nitrogen flow in 450 ml. of tetrahydrofuran at 40° C. Then, tris-(hydroxymethyl) aminomethane (378 mg., 3.12 m mole) in 15 ml of methanol are added. After stirring the mixture for 10 minutes the solvent is evaporated off under reduced pressure at 45° C. The solid residue is taken up and repeatedly washed with diethyl ether (in a total of 50 ml) on the filter. After drying under vacuum for one night at room temperature ,1.33 g of the salt of the title are obtained wherein the ratio purpuromycin:amine is 1:1.5. The salt starts to decompose at 140° C.

The $^1$H-NMR spectrum [recorded with a Bruker instrument AM 250 equipped with an Aspect 3000 console at 250 MHz at a temperature of 40° C in DMSO-$d_6$ solution (internal standard TMS, $\delta 0.00$ ] is identical to the one of purpuromycin and shows the signals of the methylenic groups of the amine ($\delta$, ppm): 3.49 (s,6H).

HPLC analysis under the following conditions:
Apparatus: Hewlett-Packard Mod 1090
Detector UV 254 nm
Flow rate 1 ml/min Column LiCrospher 100 RP-18 (5 μm)(Merck)

| Solvent A Buffer $NaH_2PO_4$ 0.02 M (pH 4.7) B acetonitrile | | | | | |
|---|---|---|---|---|---|
| linear gradient $t_{min}$ | 0 | 2 | 20 | 25 | 30 |
| % B | 35 | 35 | 50 | 50 | 35 |

The assay shows a retention time ($t_R$) of 8.5 min. which is identical to that of purpuromycin. The elemental analysis data correspond to the theoretical values for the 1:1.5 salt. The solubility of this salt in distilled water at room temperature is 4.5 mg/ml (calculated as purpuromycin). The pH value of this solution is 8.8. If the dry residue resulting from the concentration of the reaction solution is not treated with diethyl ether the product obtained has a composition corresponding to the 1:2 salt (confirmed through elemental analysis).

If the above reaction is carried out by using one molecular proportion of tris-(hydroxymethyl) aminomethane (189 mg, 1.56 mmole) instead of two, the 1:1 salt is obtained.

EXAMPLE 2

Salt of purpuromycin with L-lysine

Purpuromycin (840 mg, 1.56 mmole) is dissolved with stirring under nitrogen flow in 450 ml of tetrahydrofuran at 40° C. Then, L-lysine (456 mg, 3.12 mmole) dissolved first in a 1.5 ml of water and diluted with 20 mL of methanol, is slowly added. After stirring for 10 minutes the solvent is evaporated off under reduced pressure at 45° C. The solid residue is taken up and repeatedly washed on the filter with diethyl ether (in a total of 50 ml). After drying under vacuum for one night at room temperature, 1.48 g. of the salt of the title are obtained wherein the ratio purpuromycin:amino acid is 1:1.5. The salt starts to decompose at 140° C.

The 1H-NMR spectrum (obtained under the same conditions as in Example 1) is identical to that of purpuromycin and shows the protons signals of the amine (δ. ppm) 1.46 (m. CH$_2$); 1.53 (m. CH$_2$); 1.76 (m.CH$_2$); 2.75 (t. CH$_2$); 3.87 (m. CH).

HPLC analysis under the same conditions as in Example 1 shows a retention time (t$_R$) of 8.5.

The elemental analysis data correspond to the theoretical values for the 1:1.5 salt.

The solubility of this salt in distilled water at room temperature is 7.4 mg/ml (calculated as purpuromycin).

The pH value of a 0.5% (w/v) solution of this salt in distilled water is 8.5.

If the dry residue resulting from the concentration of the reaction solution is not treated with diethyl ether, the product obtained has the composition corresponding to the 1:2 salt (confirmed through elemental analysis).

If the above reaction is carried out by using one molecular proportion of L-lysine (228 mg. 1.56 m mole) instead of two, then the 1:1 salt is obtained.

EXAMPLE 3

Salt of purpuromycin with ethanolamine

The salt of the title is obtained by operating according to the procedure of Example 1 by substituting ethanolamine for tris-(hydroxymethyl) aminomethane. The composition of the salts (in the three different ratios) is confirmed by analytical data.

EXAMPLE 4

The following examples show some pharmaceutical topical dosage forms of pharmaceutically acceptable water soluble salts of purpuromycin for use in the treatment of infectious vaginitis. The manufacture of the dosage forms is carried out according to commonly known procedures.

Vaginal suppositories (hydrophylic)

| | |
|---|---|
| Purpuromycin 1:2 salt with lysine (micronized) (as purpuromycin) | g 0.30 |
| Methyl-decyl-sulfoxide | g 0.30 |
| Carbowax 4000 | g 1.70 |
| Carbowax 1540 | g 0.80 |
| PEG 1000 monostearate | g 1.30 |

Vaginal tablets

| | |
|---|---|
| Purpuromycin 1:1.5 salt with TRIS (micronized) (as purpuromycin) | g 0.300 |
| Lactose | g 0.096 |
| Sodium benzoate | g 0.030 |
| PVP K 30 | g 0.050 |
| Sodium bicarbonate | g 0.134 |
| Sodium citrate, acid | g 0.350 |

Anhydrous cream

| | |
|---|---|
| Purpuromycin 1:2 salt with lysine (micronized) (as purpuromycin) | g 2.00 |
| Methyl-decyl-sulfoxide | g 2.00 |
| Carbowax 6000 | g 25.00 |
| Stearyl alcohol | g 10.00 |
| Propylene glycol | g 61.00 |

Soft gelatin capsules

The capsules have an inert covering which dissolves promptly in the vagina. The covering is composed of gelatin, glycerin, water, methylparaben, propylparaben and coloring. The inside content has the following composition:

| | |
|---|---|
| Purpuromycin 1:1.5 salt with lysine or TRIS (as purpuromycin) | g 0.30 |
| Polysorbate 80 | g 0.03 |
| Cremophor ® RH80 | g 0.30 |
| Cremophor ® RH60 | g 3.47 |

Self emulsifying vaginal cream

| | |
|---|---|
| Purpuromycin 1:1.5 salt with lysine or TRIS (as purpuromycin) | g 2.00 |
| Glycerol stearate | g 11.00 |
| Stearyl alcohol | g 5.00 |
| Propylene glycol | g 10.00 |
| Cetyl alcohol | g 8.50 |
| Sorbitan monostearate | g 3.50 |
| Cremophor ® RH40 | g 60.00 |

Anhydrous gel

| | |
|---|---|
| Purpuromycin 1:1.5 salt with TRIS (as purpuromycin) | g 2.00 |
| Carboxypolymer | g 1.50 |
| Propylene glycol | g 96.50 |

Gel

| | |
|---|---|
| Purpuromycin 1:2 salt with TRIS (as purpuromycin) | g 2.00 |
| Methyl-decyl-sulfoxide | g 2.00 |
| Propylene glycol | g 8.00 |
| Carbopol 934 | g 2.00 |
| Water q.s. to | g 100 |

Vaginal foam

| | |
|---|---|
| Purpuromycin 1:1.5 salt with TRIS (as purpuromycin) | g 2.00 |
| Methyl-decyl-sulfoxide | g 2.00 |
| Octyl alcohol | g 0.87 |
| Stearyl alcohol | g 0.35 |
| Polyoxyethylene sorbitan monolaurate | g 0.23 |
| Sorbitan monolaurate | g 0.31 |
| Water | g 83.74 |
| Propellant gas | g 10.50 |

EXAMPLE 5

The following examples show some pharmaceutical dosage unit forms of pharmaceutically acceptable water soluble salts of purpuromycin for parenteral administration. Their manufacture is carried out according to commonly known procedures:

Capsules

| | |
|---|---|
| Purpuromycin 1:1.5 salt with TRIS (as purpuromycin) | mg 250 |
| Maize starch | mg 40 |
| Magnesium stearate | mg 2.5 |

Solution for infusion

| A vial with dry powder contains | | |
| --- | --- | --- |
| Purpuromycin 1:1.5 salt with L-lysine (lyophylized) (as purpuromycin) | mg | 50 |
| A vial with the solvent contains | | |
| Sodium chloride | mg | 70 |
| Water for injections q.s. to | ml | 10 |

We claim:

1. A water soluble salt of purpuromycin with an organic amine selected from (a) mono-, di- and tri- ($C_2$-$C_5$)alkyl amines wherein the alkyl group containing at least one hydrophylic substituent selected from OH, Sh, and $NH_2$ and whose pK value is comprised between 8 and 9.5, and (b) basic amino acids having a $pK_3$ value between 10 and 11.

2. A salt of claim 1 wherein the ratio between purpuromycin and the organic amine is 1:1, 1:1.5 or 1:2.

3. A salt according to claim 1 wherein the organic amine is ethanolamine, diethanolamine, tris(hydroxymethyl)aminomethane or L-lysine.

4. A purpuromycin salts of claim 1 for the topical treatment of vaginal infections.

5. A salt of purpuromycin according to claim 1 wherein said salt is ethanolamine.

6. A salt of purpuromycin according to claim 1 wherein said salt is diethanolamine.

7. A salt of purpuromycin according to claim 1 wherein said salt is tri (hydroxymethyl) aminomethane.

8. A salt of purpuromycin according to claim 1 wherein said salt is L-lysine.

9. A topical dosage form for the treatment of vaginal infections containing a water soluble salts of purpuromycin of claim 1 as the active ingredient.

10. A method for treating infectious vaginitis which comprises topically administering to a patient in need thereof an amount of the water soluble purpuromycin salts of claim 1 capable of inhibiting the growth of the microorganism causative of said infection.

11. Topical dosage form as in claim 9 wherein the vaginal infection is caused essentially by: *Candida albicans, Trichomonas vaginalis, Gardnerella vaginalis* and/or other anaerobic bacteria.

12. Method of treatment as in claim 10 where the infectious vaginitis is caused essentially by: *Candida albicans, Trichomonas vaginalis, Gardnerella vaginalis* and/or other anaerobic bacteria.

13. A liquid or semi-liquid topical dosage form according to claim 9 which contains from 0.05 to 5 per cent by weight of purpuromycin water soluble salt (calculated as purpuromycin).

14. A solid intravaginal unit dosage form according to claim 9 which contain from 10 to 600 mg, preferably from 100 to 400 mg, of water soluble purpuromycin salt (calculated as purpuromycin).

15. A method according to claim 10 and wherein the patient in need of the treatment is administered from 10 to 600 mg., preferably from 100 to 400 mg, of water soluble purpuromycin salts (calculated as purpuromycin) for each application once to three times daily.

16. A topical dosage form as in claim 9 characterized in that is formulated in an aqueous base.

17. A pharmaceutical dosage unit form for parenteral or oral administration containing as the active ingredient a water soluble purpuromycin salt of claim 1.

* * * * *

UNITED STATES PATENT AND TRADEMARK OFFICE
CERTIFICATE OF CORRECTION

PATENT NO.  : 5,118,705
DATED       : June 2, 1992
INVENTOR(S) : Aldo Trani, Sergio Bellini, Beth P. Goldstein, Luigi Simioni It is certified that error appears in the above-identified patent and that said Letters Patent is hereby corrected as shown below:

Column 1, line 19 patent reads "to a purpuromycin salts" and should read --to purpuromycin salts--.
Column 1, line 51 patent reads "was original" and should read --was originally".
Column 2, line 19 patent reads "pag." and should read --pgs.--.
Column 2, line 30 patent reads "Trichomonos" and should read --Trichomonas--.
Column 2, line 36 patent reads "83)." and should read --1983).--.
Column 9, line 67 patent reads " intended that th" and should read --intended that the--.
Column 10, lines 60-61 patent reads "pharmaceutically acceptably" and should read--pharmaceutically acceptable--.
Column 11, line 40 patent reads "hYdrophile" and should read --hydrophile--.
Column 11, line 53 patent reads "must made" and should read --must be made--.
Column 11, line 55 patent reads "pH at an undesired value" and should read --pH to an undesired value--.
Column 11, line 59 patent reads "typically contain" and should read --typically contains--.
Column 13, line 1 patent reads "shows the protons signals" and should read --shows proton signals--.
Column 15, line 15, claim 1, patent reads "group containing at" and should read --group contains at--.
Column 16, line 2, claim 9 patent reads "a water soluble salts" and should read --a water soluble salt--.

Signed and Sealed this

Thirtieth Day of November, 1993

Attest:

BRUCE LEHMAN

Attesting Officer

Commissioner of Patents and Trademarks